US011160857B2

(12) United States Patent
Moore et al.

(10) Patent No.: US 11,160,857 B2
(45) Date of Patent: Nov. 2, 2021

(54) MULTIVALENT ENTEROVIRUS VACCINE COMPOSITIONS AND USES RELATED THERETO

(71) Applicants: Emory University, Atlanta, GA (US); Children's Healthcare of Atlanta, Inc., Atlanta, GA (US)

(72) Inventors: Martin L. Moore, Decatur, GA (US); Sujin Lee, Decatur, GA (US); Minh Trang Nguyen, Warsaw (PL)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/737,239

(22) PCT Filed: Jun. 15, 2016

(86) PCT No.: PCT/US2016/037658
§ 371 (c)(1),
(2) Date: Dec. 15, 2017

(87) PCT Pub. No.: WO2016/205389
PCT Pub. Date: Dec. 22, 2016

(65) Prior Publication Data
US 2018/0169215 A1   Jun. 21, 2018

Related U.S. Application Data

(60) Provisional application No. 62/175,832, filed on Jun. 15, 2015.

(51) Int. Cl.
*A61K 39/125* (2006.01)
*A61P 31/16* (2006.01)
*A61K 39/12* (2006.01)
*A61K 39/00* (2006.01)

(52) U.S. Cl.
CPC .......... *A61K 39/125* (2013.01); *A61K 39/12* (2013.01); *A61P 31/16* (2018.01); *A61K 2039/5252* (2013.01); *A61K 2039/545* (2013.01); *A61K 2039/55505* (2013.01); *A61K 2039/70* (2013.01); *C12N 2770/32334* (2013.01)

(58) Field of Classification Search
None
See application file for complete search history.

(56) References Cited

U.S. PATENT DOCUMENTS

| | | | |
|---|---|---|---|
| 5,714,374 A | 2/1998 | Arnold | |
| 8,153,760 B2 | 4/2012 | Smith | |
| 10,080,793 B2 * | 9/2018 | van't Oever | ........... A61K 39/12 |
| 2002/0086386 A1 | 7/2002 | Kamb | |
| 2006/0088549 A1 | 4/2006 | Arnold | |
| 2011/0091501 A1 | 4/2011 | Kalnin | |
| 2012/0088814 A1 * | 4/2012 | Gregory | ............. C07K 14/7155 514/44 A |
| 2014/0161833 A1 * | 6/2014 | Kalnin | ................. A61K 39/125 424/186.1 |
| 2016/0095916 A1 | 4/2016 | McLean | |

FOREIGN PATENT DOCUMENTS

| | | |
|---|---|---|
| EP | 0257721 | 1/1992 |
| JP | 2013526617 A | 6/2013 |
| WO | 2006078648 | 7/2006 |
| WO | 2014204303 | 12/2014 |
| WO | 2015179979 | 12/2015 |

OTHER PUBLICATIONS

Buscho et al. Further Characterization of the Local Respiratory Tract Antibody Response Induced by Intranasal Instillation of Inactivated Rhinovirus 13 Vaccine, 1972, J Immun, 108(1):169.
Cain et al. Disparate adjuvant properties among three formulations of "alum", Vaccine. 2013, 31(4): 653-660.
Crowe, Universal Flu Vaccines: Primum non nocere, Sci Transl Med. 2013, 5(200):200fs34.
Edlmayr et al. Antibodies induced with recombinant VP1 from human rhinovirus exhibit cross-neutralisation, Eur Respir J, 2011; 37: 44-52.
Fox, Is a rhinovirus vaccine possible? J Epidem, 1976, 103(4), 345.
Glanville et al. Cross-Serotype Immunity Induced by Immunization with a Conserved Rhinovirus Capsid Protein, PLoS Pathog, 2013, 9(9): e1003669.
Glanville et al. Challenges in developing a cross-serotype rhinovirus vaccine, Current Opinion in Virology, 2015, 11:83-88.
Hamory et al. Human Responses to Two Decavalent Rhinovims Vaccines, The Journal of Infectious Diseases, 1975, 132(6):623.
Jacobs et al. Human Rhinovirus, Clin Microbiol Rev. 2013, 26(1):135-62.
Lee et al. A polyvalent inactivated rhinovirus vaccine is broadly immunogenic in rhesus macaques, Nat Commun. 2016, 7:12838.
Lee et al. Immunogenicity of 50-Valent Rhinovirus Vaccine, J Allergy Clin Immunol, 2017, AB376 Abstracts, L5.
Matz, Vapendavir For The Treatment Of Naturally Acquired Rhinovirus Infection In Asthmatic Adults: Effect On Asthma Control In A Phase 2 Clinical Trial, Am J Respir Crit Care Med 187;2013:A5497.
McLean et al. Rhinovirus infections and immunisation induce cross-serotype reactive antibodies to VP1, Antiviral Research 95 (2012) 193-201.

(Continued)

*Primary Examiner* — Agnieszka Boesen
(74) *Attorney, Agent, or Firm* — Emory Patent Group

(57) ABSTRACT

This disclosure relates to multivalent enterovirus vaccine compositions and uses related thereto. In certain embodiments, the disclosure relates to vaccine compositions comprising multivalent, mixtures of enterovirus (for example HRV) serotypes or recombinantly produced variants or recombinantly produced viral capsid proteins. In certain embodiments, the disclosure relates to methods of immunization comprising administering an effective amount of compositions disclosed herein to a subject diagnosed with, exhibiting symptoms of, or at risk of an enterovirus infection.

18 Claims, 7 Drawing Sheets

(56) References Cited

OTHER PUBLICATIONS

Figure 1:
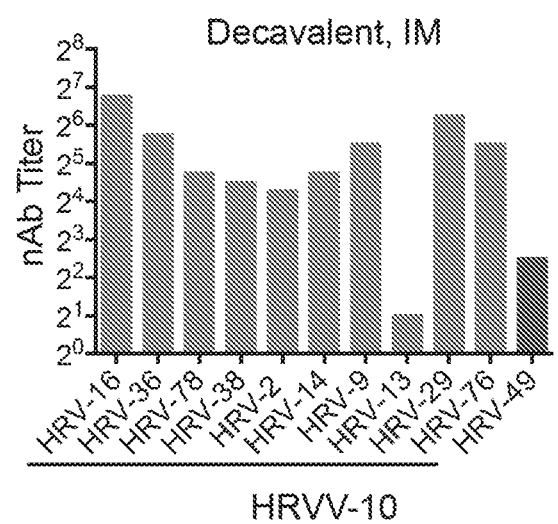

McLean, Devoloping a vaccine for human rhinoviruses, J Vaccines Immun. 2014, 2(3): 16-20.
Perkins et al. Evidence for Protective Effect of an Inactivated Rhinovirus Vaccine Administered by the Nasal Route, Am J Epidemiol. 1969, 90(4):319-26.
Pneumovax 23, Product Label, 2015.
Stott et al. Absence of Heterologous Antibody Responses in Human Volunteers after Rhinovirus Vaccination, Arch Gesamte Virusforsch. 1969, 28(1):89-92.

* cited by examiner

MULTIVALENT ENTEROVIRUS VACCINE COMPOSITIONS AND USES RELATED THERETO

CROSS-REFERENCE TO RELATED APPLICATIONS

This application is the National Stage of International Application No. PCT/US2016/037658, which claims the benefit of priority to U.S. Provisional Application No. 62/175,832 filed Jun. 15, 2015. The entirety of each of these applications is hereby incorporated by reference for all purposes.

BACKGROUND

Human rhinoviruses (HRV) are positive strand RNA viruses in the Enterovirus genus of the Picornaviridae virus family that is the most common cause of colds and the most common cause of infectious disease in man. HRV is a major cause of community-acquired pneumonia in children. The common cold is a socioeconomic burden, and rhinovirus infections can lead to serious complications in immunocompromised, aged, and young populations as well as those with chronic respiratory illnesses such as chronic obstructive pulmonary disease (COPD). Studies in human volunteers with HRV challenge and HRV vaccines demonstrated that virus-neutralizing antibodies (nAb) correlate with protection. The development of a vaccine for HRV has been hindered by the fact that over 100 serotypes have been identified. Hamory et al. reported poor human responses to two 10-valent rhinovirus vaccines [J Infect Dis. 1975, 132 (6):623-9]. Thus, there is a need to find an improved vaccination approach.

Matz reports the use of vapendavir for the treatment of naturally acquired rhinovirus infection in asthmatic adults. Am J Respir Crit Care Med, 2013, 187:A5497.

Edlmayr et al. report antibodies induced with recombinant VP1 from human rhinovirus exhibit cross-neutralization. Eur Respir J, 2011, 37:44-52.

Glanville et al. report cross-serotype T cell immunity induced by immunization with a conserved rhinovirus capsid protein. PLoS Pathog 2013, 9:e1003669. See also U.S. Published Application Numbers 2016/0095916 and 2006/0088549.

References cited herein are not an admission of prior art.

SUMMARY

This disclosure relates to multivalent enterovirus vaccine compositions and uses related thereto. In certain embodiments, the disclosure relates to vaccine compositions comprising multivalent, i.e. mixtures of human rhinovirus (HRV) serotypes, multivalent recombinantly produced HRV strains representing multiple serotypes, or multivalent recombinantly produced HRV capsid proteins representing multiple serotypes. In certain embodiments, the disclosure relates to methods of immunization comprising administering an effective amount of compositions disclosed herein to a subject diagnosed with, exhibiting symptoms of, or at risk of an HRV infection.

In certain embodiments, the disclosure relates to compositions comprising inactivated or attenuated viruses of more than 10 serotypes of the Enterovirus genus and aluminum hydroxide, aluminum phosphate, alum (potassium aluminum sulfate), or mixtures thereof, e.g., a composition comprising inactivated viruses of more than 10 serotypes of the Human rhinoviruses and an adjuvant comprising aluminum hydroxide, aluminum phosphate, alum (potassium aluminum sulfate), or mixtures thereof.

In certain embodiments, the compositions disclosed herein are in liquid form wherein each serotype is in a concentration of greater than $1\times10^3$ or $10^4$ $TCID_{50}$ per dose.

In certain embodiments, the effective amount is an immunologically effective amount, e.g., inducing a protective immune response to multiple serotypes, for more than 6, 12, 18, or 24 months.

In certain embodiments, a vaccine composition comprises more than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 HRV serotypes, recombinant variants representing serotypes, or recombinant capsid proteins representing serotypes.

In certain embodiments, the disclosure relates to compositions comprising inactivated HRVs of the following serotypes: HRV-A16, HRV-A36, HRV-A78, HRV-A38, HRV-A2, HRV-B14, HRV-A9, HRV-A29, HRV-A13, and HRV-A76. In certain embodiments, the compositions further comprise one or more serotypes of HRV-A11, HRV-A44, HRV-A60, HRV-A49, HRV-A41, HRV-A32, and HRV-A58. In certain embodiments, the compositions further comprise one or more serotypes of HRV-A33, HRV-A50, HRV-A39, HRV-B26, HRV-A21, HRV-A94, HRV-A51, HRV-A55, HRV-A45, and HRV-A1B. In certain embodiments, the compositions further comprise one or more serotypes of HRV-A100, HRV-A10, HRV-A66, HRV-A77, HRV-A40, HRV-A85, HRV-A54, HRV-A34, HRV-A24, HRV-A30, HRV-A75, HRV-A96, HRV-A19, HRV-A88, HRV-A7, HRV-A80, HRV-A68, HRV-A53, HRV-A89, HRV-A31, HRV-A56, HRV-A59, HRV-A64, and HRV-A81.

In certain embodiments, the disclosure relates to compositions comprising inactivated HRVs of the following serotypes HRV-A16, HRV-A36, HRV-A78, HRV-A38, HRV-A2, HRV-B14, HRV-A9, HRV-A13, HRV-A29, HRV-A76, HRV-A60, HRV-A49, HRV-A41, HRV-A32, HRV-A58, and HRV-A11.

In certain embodiments, the compositions further comprise one or more than 10, or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more serotypes of HRV-A1B, HRV-A2, HRV-A9, HRV-A11, HRV-B14, HRV-A16, HRV-A21, HRV-B26, HRV-A29, HRV-A32, HRV-A33, HRV-A36, HRV-A38, HRV-A39, HRV-A41, HRV-A45, HRV-A49, HRV-A50, HRV-A51, HRV-A55, HRV-A58, HRV-A60, HRV-A76, HRV-A78, HRV-A94, HRV-A7, HRV-A10, HRV-A13, HRV-A19, HRV-A24, HRV-A30, HRV-A31, HRV-A34, HRV-A40, HRV-A53, HRV-A54, HRV-A56, HRV-A59, HRV-A64, HRV-A66, HRV-A68, HRV-A75, HRV-A77, HRV-A80, HRV-A81, HRV-A85, HRV-A88, HRV-A89, HRV-A96, and HRV-A100.

In certain embodiments, the disclosure relates to inactivated HRV produced by the process of mixing a HRV serotype with cells under conditions such that the HRV infects the cells; culturing the cells in a media under conditions such that the HRV replicates, and harvesting and optionally purifying and/or concentrating the virus to provide HRV at a final concentration equal to or greater than $1\times10^6$ fifty percent tissue culture infectious dose units (TCID$_{50}$) per mL; and mixing the HRV with a HRV-inactivating agent under conditions for provide inactivated HRV.

In certain embodiments, the cells are human immortal cells or other cell lines. In certain embodiments, the culture media comprises the protein albumin.

In certain embodiments, the disclosure relates to recombinant nucleic acids encoding an infectious HRV RNA encoding a polyprotein comprising VP4, VP2, VP3, VP1, 2A, 2B, 2C, 3A, 3B, 3C, and 3D, flanked by 5' and 3' nontranslated HRV regions, wherein one, two, three, or all of the VP4, VP2, VP3, and VP1 protein sequences are from a first HRV serotype and at least one of the 2A, 2B, 2C, 3A, 3B, 3C, and 3D protein sequences are from a second HRV serotype, wherein the first HRV serotype and the second HRV serotype do not have the same serotype sequence for one, two, three, or all of the VP4, VP2, VP3, and VP1 proteins.

In certain embodiments, the second HRV serotype is HRV-A16 or HRV-A80.

In certain embodiments, the VP4, VP2, VP3, VP1, and 2A are from HRV-A36, HRV-A78, HRV-A38, HRV-A2, HRV-B14, HRV-A9, HRV-A13, HRV-A29, or HRV-A76, and the 2B, 2C, 3A, 3B, 3C, and 3D protein sequences are from HRV-A16 or HRV-A80.

In certain embodiments, the VP4, VP2, VP3, VP1, and 2A are from HRV-A11, HRV-A44, HRV-A60, HRV-A49, HRV-A41, HRV-A32, and HRV-A58, HRV-A33, HRV-A50, HRV-A39, HRV-26, HRV-A21, HRV-A94, HRV-A51, HRV-A55, HRV-A45, and HRV-A1B, HRV-A100, HRV-A10, HRV-A66, HRV-A77, HRV-A40, HRV-A85, HRV-A54, HRV-A34, HRV-A24, HRV-A30, HRV-A75, HRV-A96, HRV-A19, HRV-A88, HRV-A7, HRV-A80, HRV-A68, HRV-A53, HRV-A89, HRV-A31, HRV-A56, HRV-A59, HRV-A64, or HRV-A81, and the 2B, 2C, 3A, 3B, 3C, and 3D protein sequences are from HRV-A16 or HRV-A80.

In certain embodiments, the disclosure relates to compositions comprising vectors comprising unique nucleic acids disclosed herein, wherein each unique nucleic acid encodes a different sequence for VP4, VP2, VP3, VP1, and 2A. In certain embodiments, the compositions comprise more than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 different unique nucleic acid vectors.

In certain embodiments, the composition further comprises a nucleic acid encoding VP4, VP2, VP3, VP4, VP1, 2A, 2B, 2C, 3A, 3B, 3C, and 3D protein sequences of a single serotype.

In certain embodiments, the disclosure relates to vaccine composition comprising the inactivated naturally occurring or non-naturally occurring HRV serotypes or nucleic acid sequence disclosed herein optionally in combination with an adjuvant.

In certain embodiments, the composition further comprises recombinantly produced VP4, VP2, VP3, and/or VP1 proteins optionally in combination with an adjuvant. In certain embodiments, the compositions comprise unique capsid proteins representing more than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 different serotypes.

In certain embodiments, the disclosure relates to methods of treating or preventing a enterovirus (for example HRV) infection comprising administering an effective amount of a composition disclosed herein to a subject in need thereof.

In certain embodiments, the enterovirus is multiple human rhinoviruses that are inactivated and administered at a concentration at a concentration above or about $10^3$ or $10^4$ $TCID_{50}$ per dose.

In certain embodiments, one dose of vaccine is administered and a second dose is administered more than 3, 5, 7, 9, 11, or 13 days after the first dose.

In certain embodiments, subject is less than one or two or three or five years of age. In certain embodiments, the subject is greater than 60, 65, or 70 years of age. In certain embodiments, the subject is diagnosed with asthma, COPD, emphysema, chronic bronchitis, cystic fibrosis, or is genetically predisposed to type 1 diabetes.

In certain embodiments, the disclosure relates to multivalent vaccine compositions of other members of the Enterovirus genus such as the enterovirus species.

BRIEF DESCRIPTION OF THE FIGURES

FIG. 1 shows data on virus-neutralizing antibodies against 10 HRV serotypes induced in mice after vaccination with 10 mixed, inactivated HRV serotypes. BALB/c mice (20 per group) were vaccinated by the intramuscular route with inactivated HRVV-10. Serum was collected 18 days post-vaccination, and serum nAb titers (pooled for each group) against (left to right on the x-axis) HRV-A16, HRV-A36, HRV-A78, HRV-A38, HRV-A2, HRV-B14, HRV-A9, HRV-A13, HRV-A29, HRV-A76, and HRV-A49 were quantified by $TCID_{50}$ reduction assay in HeLa cells. The serotypes included in the vaccines are indicated in the graph by the black line. HRVV-10 induced nAb against 9 of the 10 input serotypes (not HRV-A13), and HRVV-10 induced nAb against HRV-A49, a serotype not included in the vaccine but in the same antigenic group as HRV-A2.

FIG. 2 illustrates a bacterial artificial chromosome (BAC) vector comprising a HRV nucleic acid that produces infectious HRV. The diagram illustrates a HRV-A16 construct cloned into a BAC vector. This HRV-A16 nucleic acid is immediately flanked by 5' and 3' ribozymes, and expression is driven by a 5' T7 promoter. The HRV-A16 BAC has engineered Sac I and Cla I restriction enzyme sites flanking the capsid genes which enables the engineering and rescue of capsid-chimeric HRV. The vector serves as a template for in vitro T7 transcription. The RNA produced is transfected into HeLa cells, and infectious HRV is readily produced.

FIG. 3A shows data indicating the immunogenicity of inactivated HRV-A16 is not affected by increasing valency from one to ten. Mice were vaccinated i.m. with 1-valent inactivated HRV-A16 with or without alum adjuvant (5 mice per group) or with 3-valent, 5-valent, 7-valent, or 10-valent inactivated HRV with alum (20 mice per group). HRV types and inactivated-$TCID_{50}$ doses are specified in Supplemental Table 1. Sera were collected 18 days after vaccination and pooled for each group. Serum nAb titers were measured against HRV-A16, HRV-A36, and HRV-A78. The dashed line represents limit of detection (LOD).

FIG. 3B shows data for HRV-A36.

FIG. 3C shows data of HRV-A78.

FIG. 4A shows data indicating immunogenicity of inactivated polyvalent HRV is related to dose. Mice (2 groups, 20 per group) were vaccinated with 10-valent HRV vaccine consisting of low inactivated-TCID$_{50}$ per dose input titers (x-axis), similar to the 1975 Hamory et al. study 10, plus alum (gray symbols) or with 10-valent HRV vaccine with high inactivated-TCID$_{50}$ per dose input titers plus alum (black symbols). Sera were collected 18 days after prime, pooled for each group, and nAb titers (y-axis) were measured against the indicated types in the vaccines. The dashed line represents LOD. Undetectable nAb were assigned LOD/2, and some symbols below LOD were nudged for visualization.

Figure 4A:
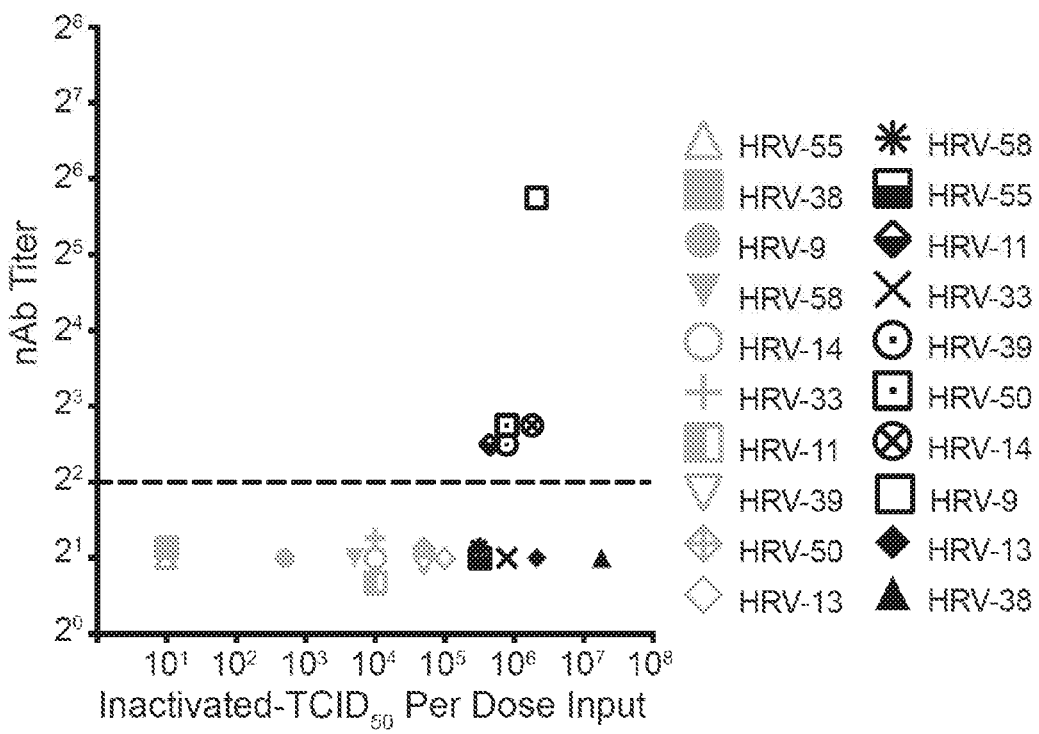
Figure 4B:
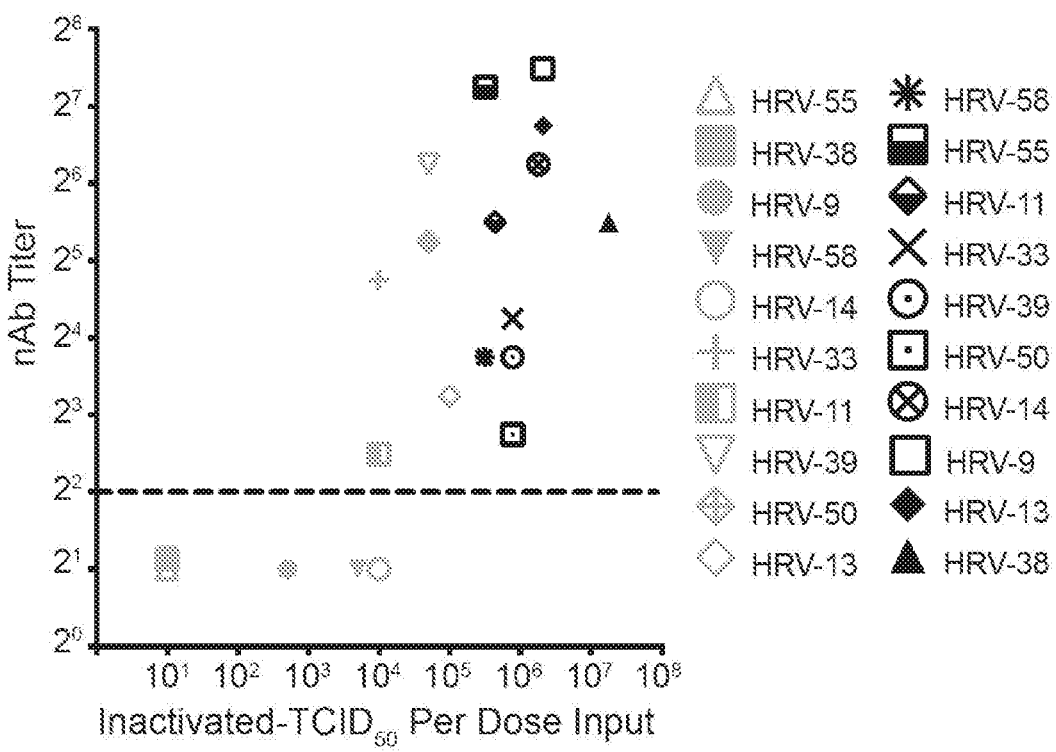

FIG. 4B shows data 18 days after boost.

Figure 5A:
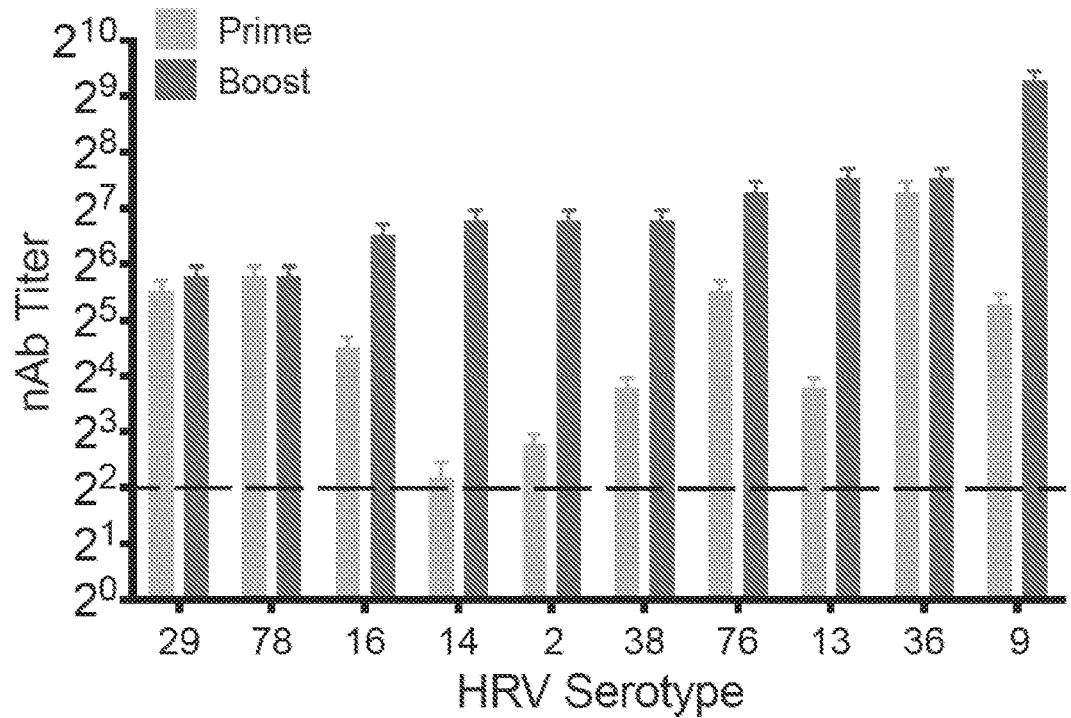

FIG. 5A shows data indicating broad nAb responses against 10-valent and 25-valent inactivated HRV in mice. The inactivated-TCID$_{50}$ input titers per dose are specified in the Table 5. 20 mice were vaccinated then boosted at 50 days with 10-valent HRV. Sera were collected at day 18 (prime) and day 68 (boost). nAb levels against the indicated types in the vaccines were measured in pooled sera. The dashed line represents LOD. Undetectable nAb were assigned LOD/2.

Figure 5B:
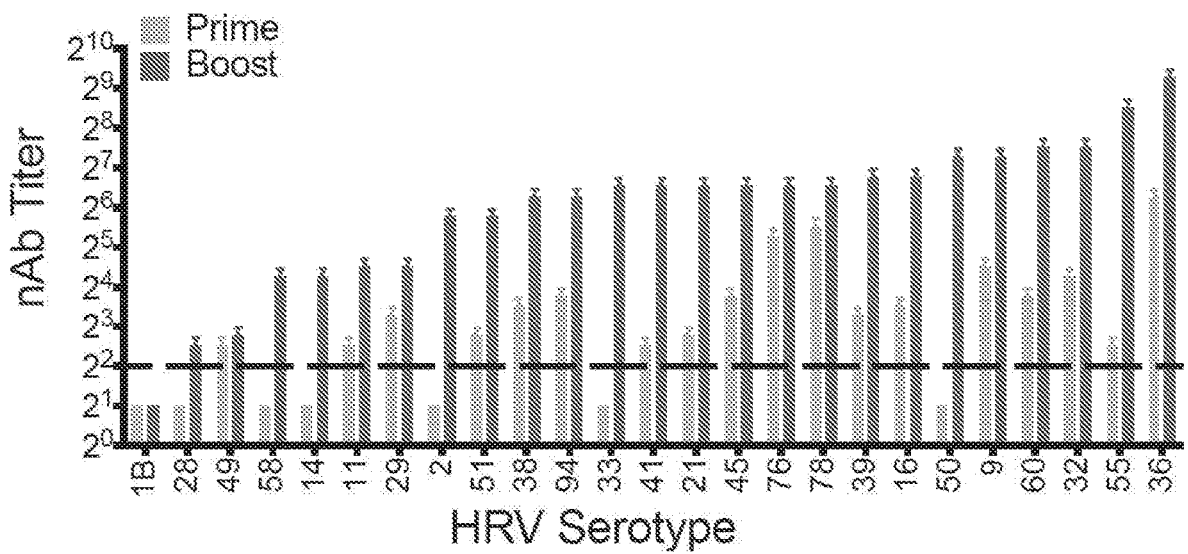

FIG. 5B shows data for 30 mice vaccinated then boosted at 50 days with 25-valent HRV.

Figure 6A:
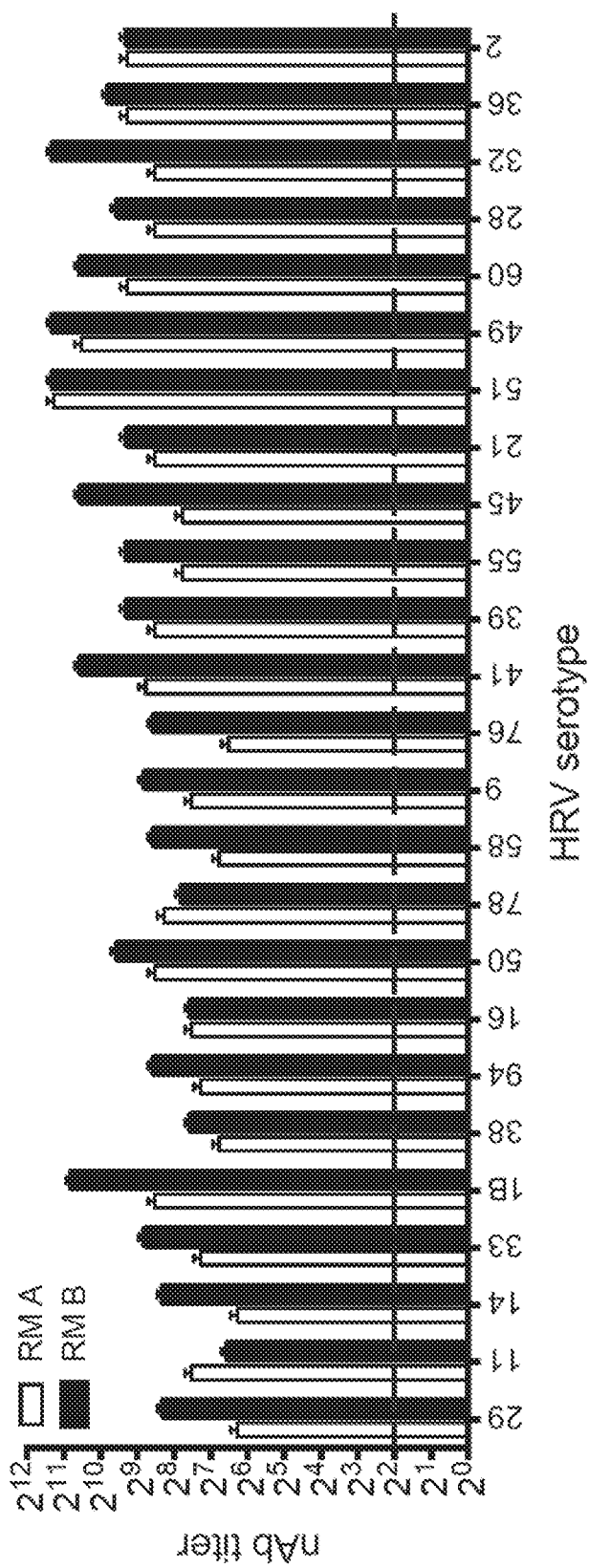

FIG. 6A shows data indicating a broad nAb responses against 25-valent inactivated HRV in rhesus macaques after a prime and boost. The inactivated-TCID$_{50}$ input titers per dose are specified in Table 6. Two rhesus macaques (RM A and RM B) were vaccinated i.m. with 25-valent HRV+alum. The RM received an identical boost vaccination at day 28, and sera were collected at day 46 for determining nAb titers post-boost vaccination. The dashed line represents LOD. Undetectable nAb were assigned LOD/2.

Figure 6B:
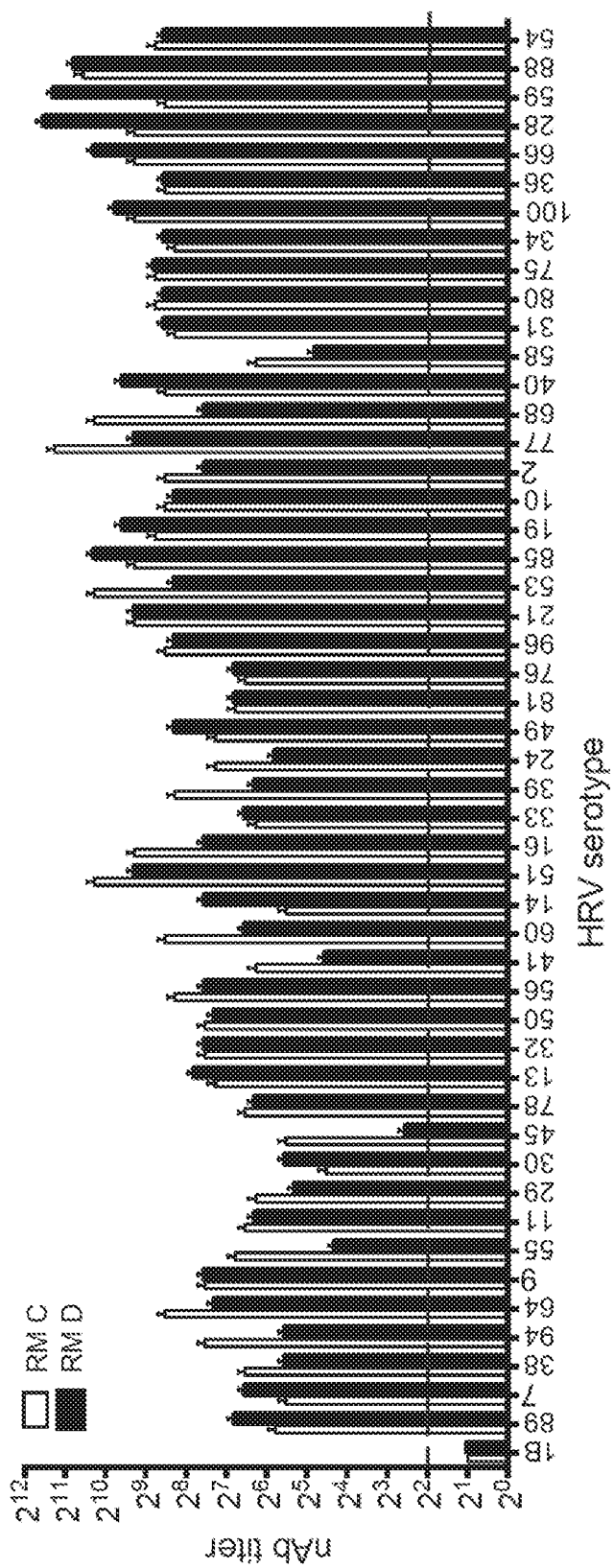

FIG. 6B shows data where two rhesus macaques (RM C and RM D) were vaccinated i.m. with 50-valent HRV+alum after a prime and boost.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The term "rhinovirus" or "HRV" (Human rhinovirus) refers to any member of the family Picornaviridae genus Enterovirus according to the recent taxonomy. There are 3 different species of rhinoviruses: Human rhinovirus A (HRV-A) also called type A rhinovirus, Human rhinovirus B (HRV-B) also called type B rhinovirus and Human rhinovirus C (HRV-C) also called type C rhinovirus.

HRVs are further classified according to their serotype, of which more than 150 have been reported.

As used herein, the term "serotype" refers to a subdivision within a group of rhinoviruses and relies on the VP1 gene sequence of the rhinovirus. A given serotype of rhinovirus may contain one or several strains that are distinguished by secondary characteristics. HRVs have been classified according to several other parameters, including receptor specificity, antiviral susceptibility and nucleotide sequence homologies. The HRV-A species includes in particular the following 83 serotypes: HRV-A1A, HRV-A1B, HRV-A2, HRV-A7, HRV-A8, HRV-A9, HRV-A10, HRV-A11, HRV-A12, HRV-A13, HRV-A15, HRV-A16, HRV-A18, HRV-A19, HRV-A20, HRV-A21, HRV-A22, HRV-A23, HRV-A24, HRV-A25, HRV-A27, HRV-A28, HRV-A29, HRV-A30, HRV-A31, HRV-A32, HRV-A33, HRV-A34, HRV-A36, HRV-A38, HRV-A39, HRV-A40, HRV-A41, HRV-A43, HRV-A44, HRV-A45, HRV-A46, HRV-A47, HRV-A49, HRV-A50, HRV-A51, HRV-A53, HRV-A54, HRV-A55, HRV-A56, HRV-A57, HRV-A58, HRV-A59, HRV-A60, HRV-A61, HRV-A62, HRV-A63, HRV-A64, HRV-A65, HRV-A66, HRV-A67, HRV-A68, HRV-A71, HRV-A73, HRV-A74, HRV-A75, HRV-A76, HRV-A77, HRV-A78, HRV-A80, HRV-A81, HRV-A82, HRV-A85, HRV-A88, HRV-A89, HRV-A90, HRV-A94, HRV-A96, HRV-A100, HRV-A101, HRV-A102, HRV-A103, HRV-A104, HRV-A105, HRV-A106, HRV-A107, HRV-A108, and HRV-A109; the HRV-B species includes in particular the following 32 serotypes: HRV-B3, HRV-B4, HRV-B5, HRV-B6, HRV-B14, HRV-B17, HRV-B26, HRV-B27, HRV-B35, HRV-B37, HRV-B42, HRV-B48, HRV-B52, HRV-B69, HRV-B70, HRV-B72, HRV-B79, HRV-B83, HRV-B84, HRV-B86, HRV-B91, HRV-B92, HRV-B93, HRV-B97, HRV-B99, HRV-B100, HRV-B101, HRV-B102, HRV-B103, HRV-B104, HRV-B105, and HRV-B106; and the HRV-C species includes in particular the following 55 serotypes: HRV-C1, HRV-C2, HRV-C3, HRV-C4, HRV-05, HRV-C6, HRV-C7, HRV-C8, HRV-C9, HRV-C10, HRV-C11, HRV-C12, HRV-C13, HRV-C14, HRV-C15, HRV-C16, HRV-C17, HRV-C18, HRV-C19, HRV-C20, HRV-C21, HRV-C22, HRV-C23, HRV-C24, HRV-C25, HRV-C26, HRV-C27, HRV-C28, HRV-C29, HRV-C30, HRV-C31, HRV-C32, HRV-C33, HRV-C34, HRV-C35, HRV-C36, HRV-C37, HRV-C38, HRV-C39, HRV-C40, HRV-C41, HRV-C42, HRV-C43, HRV-C44, HRV-C45, HRV-C46, HRV-C47, HRV-C48, HRV-C49, HRV-050, HRV-051, HRV-052, HRV-053, HRV-054, and HRV-055.

HRV serotypes may also be grouped according to receptor usage into minor-group viruses and major-group viruses.

Minor-group viruses, such as HRV-A2, use the low-density lipoprotein receptor family as receptor. They are acid labile and have an absolute dependence on low pH for uncoating. Major-group viruses, such as HRV-B14 and HRV-A16, use intercellular adhesion molecule 1 (ICAM-1) as receptor. They are also generally acid labile but, unlike the minor-group viruses, do not have an absolute dependence on low pH for uncoating.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

The term "nucleic acid" refers to a polymer of nucleotides, or a polynucleotide. The term is used to designate a single molecule, or a collection of molecules. Nucleic acids may be single stranded or double stranded, and may include coding regions and regions of various control elements, as described below.

The term "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. Recombinant vectors typical contain selectable markers.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: $amp^r$, $cam^r$, $tet^r$, $blasticidin^r$, $neo^r$, $hyg^r$, $abx^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

In certain embodiments, the disclosure relates to the recombinant vectors comprising a nucleic acid encoding a HRV polyprotein disclosed herein or chimeric protein thereof. The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequence includes those obtained from the same or from different viral serotypes.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one viral serotype introduced into another serotype. A heterologous gene also includes a gene native to an organism that has been altered in some way (e.g., mutated, added in multiple copies, linked to a non-native promoter or enhancer sequence, etc.). Heterologous genes may comprise virus gene sequences that comprise cDNA forms of a virus gene; the cDNA sequences may be expressed in either a sense (to produce mRNA) or anti-sense orientation (to produce an anti-sense RNA transcript that is complementary to the mRNA transcript). Heterologous genes are distinguished from endogenous virus genes in that the heterologous gene sequences are typically joined to nucleotide sequences comprising regulatory elements such as promoters that are not found naturally associated with the gene for the protein encoded by the heterologous gene or with virus gene sequences in the chromosome, or are associated with portions of the chromosome not found in nature (e.g., genes expressed in loci where the gene is not normally expressed).

The term "transfection" refers to the introduction of foreign nucleic acid into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection of DNA or RNA, protoplast fusion, viral infection, biolistics (i.e., particle bombardment) and the like.

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

An "immunologically effective amount" is an amount sufficient to enhance an individual's (e.g., a human's) own immune response against the input antigen and/or provide protection against subsequent exposure. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" refers to an immune response exhibited by an individual (e.g., a human) that is protective against upper and/or lower respiratory tract disease (e.g., a cold and/or pneumonia) when the individual is subsequently exposed to and/or infected.

Human Rhinovirus (HRV) and Vaccines

HRV has positive sense RNA genome. The RNA contains 5' and 3' nontranslated regions (NTR) having a 3'-terminal poly(A) tail with an open reading frame encoding a single polyprotein. Virion RNA and synthetic genome-length RNA derived from recombinant cDNA clones are infectious when transfected into cells, giving rise to virus particles and subsequent rounds of virus replication. See Yang et al. [J Virol, 2002, 76:7485]. The 5'-NTR has internal ribosome entry site but lacks the 5'-terminal cap structure of mRNAs, thus cellular translational bypasses a 5' encoded viral protein (VPg).

The polyprotein contains three segments related to the order of cleavage by viral proteases. N-terminal segment, P1, contains four capsid proteins, VP4, VP2, VP3, and VP1. VP2, VP3, and VP1 are exposed on the exterior of the capsid. The P2 and P3 segments are comprised of nonstructural proteins. These include 2A (protease), 2B, 2C, 3A, 3B(VPg), 3C (protease), and 3D (polymerase). Precursors include 2BC, 3AB, and 3CD.

HRV is in the Enterovirus genus of the Picornaviridae family and referred to by numbered serotype. There are three species of HRVs, A, B, and C. Cooney et al. report antigenic groupings of 90 rhinovirus serotypes. Infect Immun 37, 642-647 (1982). There are antigenic groups of HRV serotypes that exhibit cross-neutralization, with some serotype pairings exhibiting reciprocal neutralization using high titer anti-sera generated in animals. The molecular epidemiology of HRVs shows the serotypes are numerous but stable, and "antigenic drift" does not occur in HRV as it does in influenza.

U.S. Published Patent Application number 2010/0233677 reports the genomic sequences of 80 human rhinoviruses (HRVs). Genome sequences for certain serotypes are referenced in the Table 1 below.

TABLE 1 provides the serotype sequences on public databases

| Virus Serotype | RNA sequences (NCBI accession numbers in public database) | Virus Serotype | RNA sequences (NCBI accession numbers in public database) |
|---|---|---|---|
| HRV-A16 | L24917.1 | HRV-A32 | FJ445127.1 |
| HRV-A36 | DQ473505.1 | HRV-A58 | FJ445142.1 |
| HRV-A78 | EF173418.1 | HRV-A33 | FJ445128.1 |
| HRV-A38 | DQ473495.1 | HRV-A50 | FJ445135.1 |
| HRV-A2 | X02316.1 | HRV-A39 | AY751783.1 |
| HRV-B14 | NC_001490.1 | HRV-B26 | DQ473508.1 |
| HRV-A9 | FJ445177.1 | HRV-A21 | FJ445121.1 |
| HRV-A29 | FJ445125.1 | HRV-A94 | FJ445185.1 |
| HRV-A76 | FJ445182.1 | HRV-A51 | FJ445136.1 |
| HRV-A44 | DQ473499.1 | HRV-A55 | DQ473511.1 |
| HRV-A60 | FJ445143.1 | HRV-A45 | FJ445132.1 |
| HRV-A49 | DQ473496.1 | HRV-A1B | D00239.1 |
| HRV-A41 | DQ473491.1 | | |

Mixing inactivated HRV strains or assembled, empty capsid proteins of the strains, e.g., equal to or greater than 10, 15, 20, 25, 30, 35, 40, 45, 50 or more serotypes represented, may elicit a protective neutralizing antibody (nAb) response to a substantial number of HRV types. Disclosed herein are multivalent HRV vaccines optionally in combination with a desirable adjuvant. In certain embodiments, the HRV compositions comprise inactivated HRV of more than 9 serotypes and methods contemplating intranasal (i.n) or intramuscular (i.m) administration.

Infections in otherwise healthy adults cause symptoms of the common cold. Thus in certain embodiments, this disclosure relates to methods of preventing HRV infection by administering compositions disclosed herein to a subject on a periodic or routine schedule, e.g., every six months, every one or two years or longer. Respiratory virus infections have been associated with a high percentage of exacerbations of asthma and chronic obstructive pulmonary disease (COPD). Thus in certain embodiments, the disclosure relates to managing or preventing exacerbations of obstructed airway conditions and diseases comprising administering compositions disclosed herein to a subject diagnosed with, exhibiting symptoms of, or at risk of an obstructed airway condition such as pulmonary exacerbations of asthma, COPD, emphysema, chronic bronchitis, or cystic fibrosis ("CF").

HRV C infection is associated with severe respiratory illness in children. Thus, in certain embodiments, this disclosure relates to treating or preventing HRV infections comprising administering compositions disclosed herein, e.g., compositions containing a HRV C serotype or recombinant virus as an attenuated or inactivated (killed) virus, or recombinant HRV C capsid proteins.

HRV infections in early life may be associated with development of asthma later in childhood. Thus, in certain embodiments, this disclosure contemplates preventing asthma comprising administering compositions disclosed herein to a child of less than two, three, four, five, or six months of age, or between two months and six months, between six months and a year, or more than a year old.

In certain embodiments, the disclosure contemplates recombinantly produced capsid-chimeric HRV, i.e., produced from an HRV RNA that encodes heterologous proteins, e.g., wherein at least one VP4, VP2, VP3, or VP1 capsid protein are sequences of a first serotype of HRV and at least one non-capsid protein such as 2A, 2B, 2C, 3A, 3B, 3C and/or 3D are sequences of a second serotype and the first and second serotype are not of the same serotype, as they are different, e.g., VP4, VP2, VP3, VP1, and 2A are of HRV-A2 and the rest of the proteins are of HRV-A16 or HRV-A80.

In certain embodiments, any of the compositions disclosed herein may contain other antiviral agents such as abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), zidovudine, and/or vapendavir, derivatives or salts thereof.

Biota pharmaceuticals is studying the use of vapendavir in asthmatic adults with symptomatic human rhinovirus infection. Matz, Am J Respir Crit Care Med, 187, 2013:A5497. Vapendavir (3-ethoxy-6-(2-(1-(6-methylpyridazin-3-yl)piperidin-4-yl)ethoxy)benzo[d]isoxazole) is a capsid binder that has antiviral activity. The mechanism of action is believed to interfere with early steps in the infectious cycle.

In certain embodiments, any of the compositions disclosed herein may be used for any of the methods disclosed herein wherein other antiviral agents, e.g., vapendavir, derivatives or salts thereof are administered in combination. Thus, in some embodiments, the disclosure relates to preventing or treatment patients with underlying respiratory illnesses, including moderate to severe asthma and chronic obstructive pulmonary disease optionally infected with HRV by administering compositions comprising killed, inactivated virus, attenuated virus, VP4, VP2, VP3, and VP1 proteins, HRV serotypes and/or recombinant HRVs disclosed herein in combination with other antiviral agents such as vapendavir or derivatives or salts thereof.

Virus Quantification

TCID$_{50}$ refers to 50% tissue culture infective dose. It is a standard measure of infectious virus titer. This endpoint dilution assay quantifies the amount of virus required to produce a cytopathic effect (CPE) in 50% of inoculated tissue culture cells. When used in the context of tissue culture, host cells are plated and serial dilutions of the virus are added. After incubation, the percentage of cell death (i.e. infected cells) is manually observed and recorded for each virus dilution, and results are used to mathematically calculate a TCID$_{50}$ result. The Reed and Muench method [Reed and Muench, Am. J. Hyg, 1938, 27: 493] can be used to calculate the TCID$_{50}$ end point titers. Briefly, the TCID$_{50}$ method allows one to add the total number of virus positive wells from a plate of tissue culture cells (e.g. HeLa cells) infected with serial dilutions of virus, and convert the data to a titer that represents an endpoint (the tissue culture infectious dose is 50% at this point). The following formula is used to perform the calculation:

Proportionate Distance=(% CPE at dilution above 50%)−(50%) (% CPE at dilution above 50%)−(% CPE at dilution below 50%)     i.

−Log=dilution above 50% CPE ratio (i.e. $10^{-3}$ would be −3)     ii.

((PD)+(−log(dilution interval)))     iii.

TCID$_{50}$=$10^{(ii+iii)}$     iv.

Administration and Dosage

In certain embodiments, this disclosure relates to compositions that include prophylactically or therapeutically effective amounts of one or more HRV vaccines, as described herein. The mixtures of HRV vaccines may be present in the same pharmaceutical composition (a single dosage form) or separate pharmaceutical compositions (separate dosage forms), which are administered concomitantly or at different times. The compositions can be formulated for use in a variety of drug delivery systems. One or more physiologically acceptable excipients or carriers can also be included in the compositions for proper formulation. The viruses can be in lyophilized form or dissolved in a physiologically compatible solution or buffer, such as saline or water. Standard methods of preparation and formulation can be used as described, for example, in Remington's Pharmaceutical Sciences (18$^{th}$ edition), ed. A. Gennaro, 1990, Mack Publishing Company, Easton, Pa.

For vaccine use, virus produced according to the present disclosure can be used directly in vaccine formulations, or lyophilized, as desired, using lyophilization protocols well known to the artisan. Lyophilized virus will typically be maintained at about 4 degrees C. When ready for use the lyophilized virus is reconstituted in a stabilizing solution, e.g., saline or comprising SPG, Mg, and HEPES, with or without adjuvant, as further described below.

The modified, attenuated, inactivated virus, or recombinant virus capsids may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum.

The compositions are intended for intranasal, parenteral, topical, oral, or local administration for prophylactic and/or therapeutic treatment. Typically, the compositions are administered intranasally (e.g., by aerosol inhalation or nose drops), parenterally (e.g., by intramuscular, subcutaneous, or intravenous injection), or by oral ingestion, or by topical application or intraarticular injection. Additional routes of administration include intravascular, intra-arterial, intratumor, intraperitoneal, intraventricular, intraepidural, as well as ophthalmic, intrascleral, intraorbital, rectal, or topical administration. Sustained release administration is also specifically included in the disclosure, by such means as depot injections or erodible implants or components. Thus, the disclosure provides compositions for mucosal or parenteral administration that include the above-mentioned agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is or lyophilized, the lyophilized preparation being combined with a sterile aqueous carrier prior to administration. The pH of the preparations typically will be between 3 and 11, e.g., between 5 and 9, 6 and 8, or 7 and 8, such as 7 to 7.5. The resulting compositions in solid form may be packaged in multiple single dose units, each containing a fixed amount of the above-mentioned agent or agents, such as in a sealed package of tablets or capsules. The compositions can also include the active ingredient(s) in lyophilized form, which is reconstituted for administration.

The compositions containing an effective amount of vaccine can be administered for prophylactic and/or therapeutic treatments. In prophylactic applications, compositions can be administered to a subject (e.g., a human subject) with increased susceptibility to HRV infection. Compositions of the disclosure will be administered to the subject (e.g., a human) in an amount sufficient to delay, reduce, or prevent the onset of clinical or subclinical disease. In therapeutic applications, compositions are administered to a patient (e.g., a human) already suffering from HRV infection in an amount sufficient to cure or at least partially arrest the symptoms of the condition and its complications. An amount adequate to accomplish this purpose is defined as a "therapeutically effective dose." Determination of an appropriate dosage amount and regimen can readily be determined by those of skill in the art. Amounts effective for this use may depend on the severity of the disease or condition and the weight and general state of the patient, but generally range from about 0.5 mg to about 3000 mg of the agent or agents per dose per patient.

The vaccines can be administered one time only or in prime/boost regimens. Suitable regimens for initial administration and booster administrations are typified by an initial administration followed by repeated doses at one or more hourly, daily, weekly, or monthly intervals by a subsequent administration. The total effective amount of an agent present in the compositions of the disclosure can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month).

The therapeutically-effective amount of one or more agents present within the compositions of the disclosure and used in the methods of this disclosure applied to mammals (e.g., humans) can be determined by the those of skill in the art with consideration of individual differences in age, weight, immune system integrity, and the condition of the mammal. The agents of the disclosure are administered to a subject (e.g. a mammal, such as human, mouse, livestock (e.g., cattle, sheep, or pigs), domestic pet (e.g., cat or dog) in an effective amount, which is an amount that produces a desirable result in a treated subject (e.g., the prevention of HRV infection in a susceptible individual or the lessening of symptoms in an infected individual). Such therapeutically effective amounts can be determined empirically by those of skill in the art.

The vaccines of the disclosure can be used in combination with other vaccination approaches, as well as other approaches to treatment (e.g., small molecule-based approaches). For example, the viruses can be administered in combination with other recombinant vaccines including the same or different antigens. The combination methods of the disclosure can include co-administration of vaccines of the disclosure with other forms of the antigen. Alternatively, the vaccines of the present disclosure can be used in combination with other approaches (such as subunit or HBc approaches (HBc-M2e; Fiers et al., Virus Res. 103:173-176, 2004; WO 2005/055957; US 2003/0138769 A1; US 2004/0146524A1; US 2007/0036826 A1)) in a prime-boost strategy, with either the vaccines of the disclosure or the other approaches being used as the prime, followed by use of the other approach as the boost, or the reverse. Further, the disclosure includes prime-boost strategies employing the vaccine of the present disclosure as both prime and boost agents.

The vaccines of the disclosure can be administered to subjects, such as mammals (e.g., human subjects) using standard methods. In the case of intranasal administration, the compositions can be administered in the form of nose-drops or by inhalation of an aerosolized or nebulized formulation.

The compositions of the disclosure can be administered to subjects, such as humans, as live or killed vaccines or assembled capsid proteins. The live attenuated vaccines can be administered intranasally using methods known to those of skill in the art (see, e.g., Grunberg et al., Am. J. Respir. Crit. Car. Med. 156:609-616, 1997). Appropriate dosage amounts and regimens can readily be determined by those of skill in the art. As an example, the dose range can be, e.g., $10^4$ to $10^9$ $TCID_{50}$ per dose. The vaccine can advantageously be administered in a single dose, however, boosting can be carried out as well, if determined to be necessary by those skilled in the art. As to inactivated vaccines, the virus can be killed with, e.g., formalin or UV or beta-propiolactone treatment, and administered intranasally or intramuscularly at about $10^{4-9}$ equivalent $TCID_{50}$ per dose, optionally with appropriate adjuvant (e.g., aluminum). In such approaches, it may be advantageous to administer more than one (e.g., 2-3) dose. Recombinantly produced capsid proteins can be similarly administered intranasally or intramuscularly, optionally with appropriate adjuvant, using one or more doses.

Adjuvants

For vaccine applications, optionally, adjuvants that are known to those skilled in the art can be used. In the case of intranasal administration, chitin microparticles (CMP) can be used (Asahi-Ozaki et al., Microbes and Infection 8:2706-2714, 2006; Ozdemir et al., Clinical and Experimental Allergy 36:960-968, 2006; Strong et al., Clinical and Experimental Allergy 32:1794-1800, 2002). Other adjuvants suitable for use in administration via the mucosal route (e.g., intranasal or oral routes) include the heat-labile toxin of *E. coli* (LT) or mutant derivatives thereof. In the case of inactivated virus and capsid proteins, parenteral adjuvants can be used including, for example, aluminum compounds (e.g., an aluminum hydroxide, aluminum phosphate, or aluminum hydroxyphosphate compound), liposomal formulations, synthetic adjuvants, such as (e.g., QS21), muramyl dipeptide, monophosphoryl lipid A, or polyphosphazine. In addition, genes encoding cytokines that have adjuvant activities can be inserted into the vectors. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses. Alternatively, cytokines can be delivered, simultaneously or sequentially, separately from a recombinant vaccine virus by means that are well known (e.g., direct inoculation, naked DNA, in a viral vector, etc.).

EXAMPLES

Figure 2:
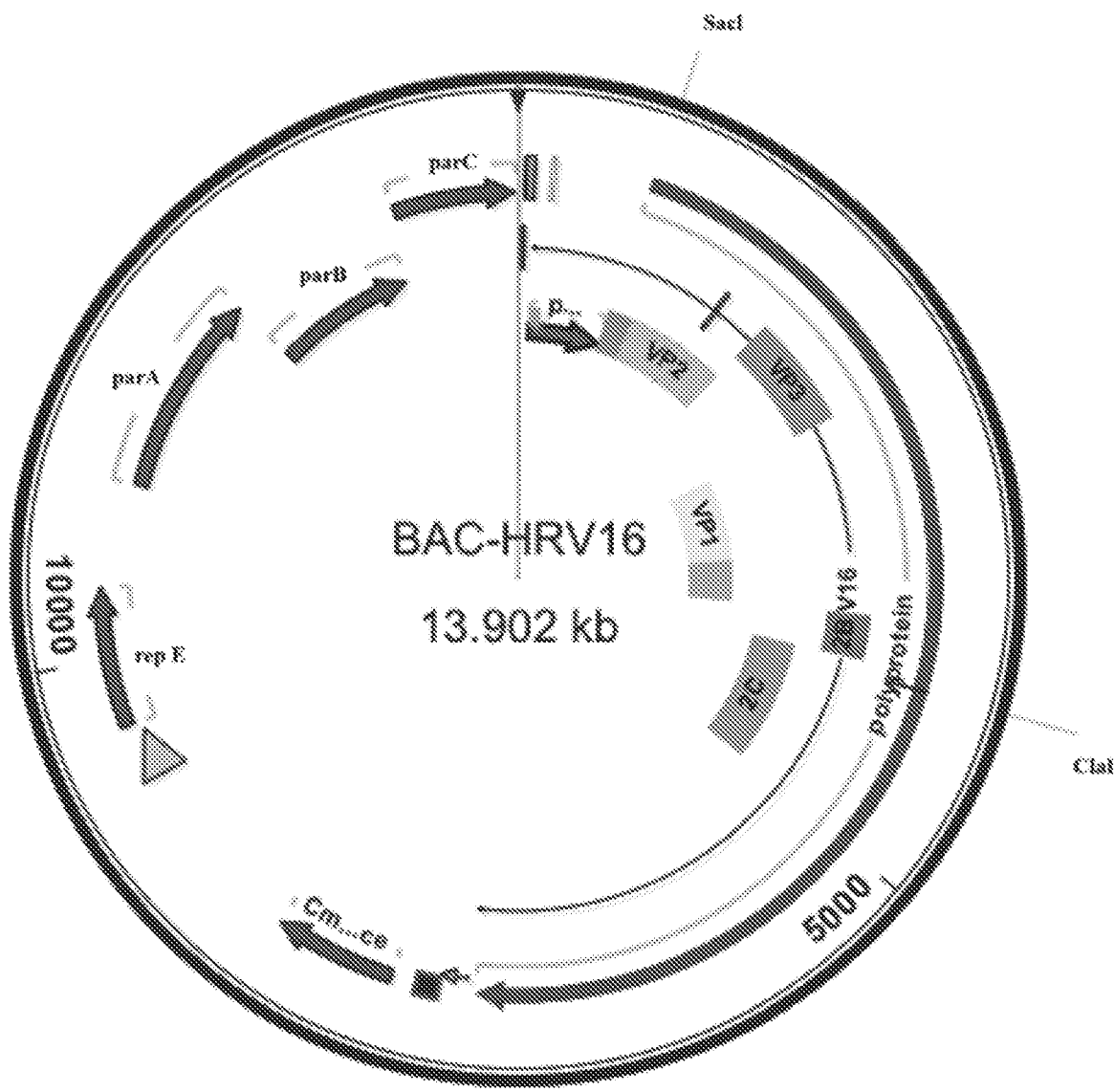
Figure 3A:
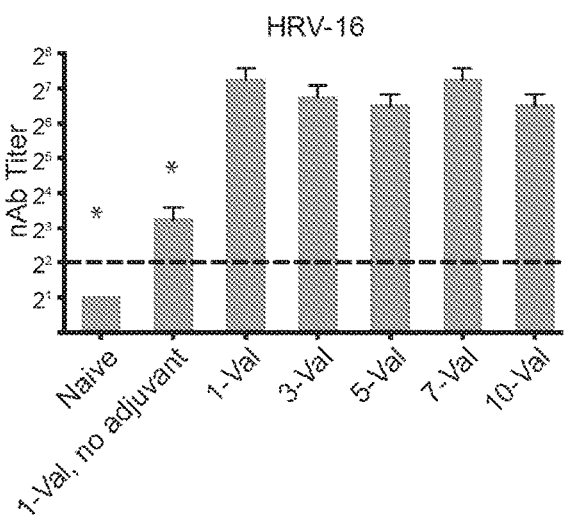
Figure 3B:
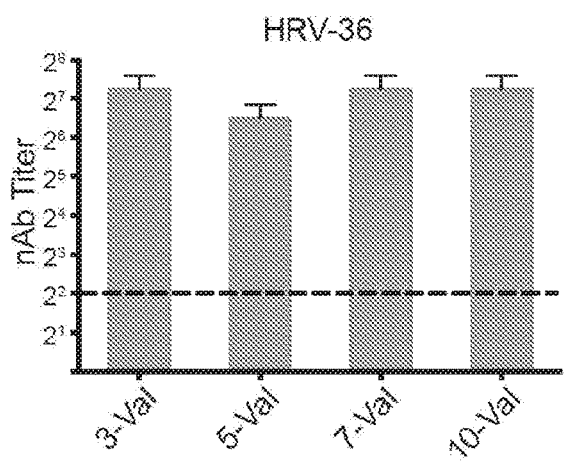
Figure 3C:
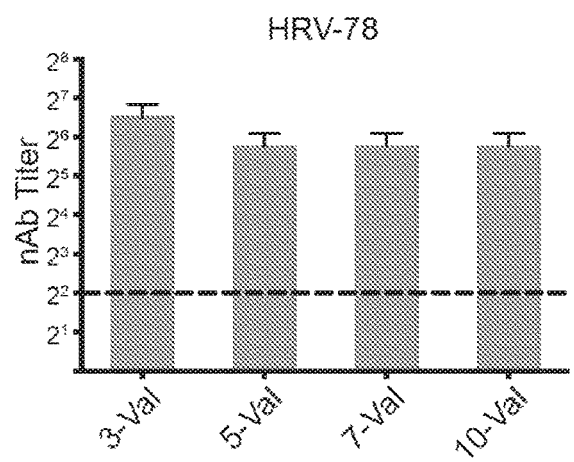

The major hurdle in developing a HRV vaccine is the number of serotypes (>100). It has been discovered that the number of HRV serotypes can be overcome, in part, using methods disclosed herein. One concern about combining vaccines (multivalency) is that unique antigens will compete with or interfere with each other. It was discovered this was not the case because inactivated HRV serotypes were equally immunogenic in mice when given in monovalent, 3-valent, 5-valent, 7-valent, or 10-valent compositions (FIGS. 1 and 2). Furthermore, ten HRV high titer reference serotype strains (Table 2) are co-mixed to generate HRVV-10. HRVV-10 elicits serum nAbs in mice against 10 HRV serotypes (FIG. 3).

TABLE 2

HRV serotypes included in HRVV-10

| Serotype | $TCID_{50}$/ml titer of P2 virus stock prior to inactivation |
|---|---|
| HRV-A16 | $7.5 \times 10^8$ |
| HRV-A36 | $6.3 \times 10^8$ |
| HRV-A78 | $6.3 \times 10^7$ |
| HRV-A38 | $1.1 \times 10^8$ |
| HRV-A2 | $1.3 \times 10^9$ |
| HRV-B14 | $6.6 \times 10^8$ |
| HRV-A9 | $3.6 \times 10^8$ |
| HRV-A13 | $6.3 \times 10^7$ |
| HRV-A29 | $3.6 \times 10^7$ |
| HRV-A76 | $3.6 \times 10^7$ |

HRV Stocks

HRV prototype strains were purchased from the American Type Culture Collection (ATCC) and propagated by in H1-HeLa cells (ATCC) in T-75 cm² flasks. At the peak of cytopathic effects, the cells were scraped in media, sonicated, the cell debris clarified, and 50 mL supernatant aliquoted and snap-frozen in liquid nitrogen. Infectivity was titrated by crystal violet staining of infected H1-HeLa cells in 96-well plates. The $TCID_{50}$ titers of passage #1 (P1) stocks were calculated using Reed and Muench end-point dilution.

Concentrated-titer P2 stocks are generated by infecting H1-HeLa cells in media without phenol red in 10 T-182 cm² flasks with P1 stock. Prior to the peak of infection, 45 mL of media are discarded from each flask, and the cells scraped in the remaining 5 mL, sonicated, the debris clarified, and the 5 mL supernatants pooled into two 25 mL aliquots and snap-frozen. A concentrated HRV-A16 P2 stock was generated by this method and achieved a 10-fold increase in titer over the P1 stock.

The monovalent HRV vaccine produced by Abbott Labs in 1964 and tested by Chanock, which worked in volunteers against homologous-strain challenge, contained approximately $10^{5.5}$ equivalent $TCID_{50}$ per dose of inactivated HRV-A13, and this vaccine induced nAb in human subjects [Buscho et al. (1972) J. Immunol. 108: 169]. The two 10-valent inactivated HRV vaccines that failed had mean input titers of $10^{3.3}$ equivalent $TCID_{50}$ per dose of the 10 serotypes [Hamory et al. J Infect Dis. 1975, 132(6):623-9]. Neither the monovalent nor the 10-valent human vaccines were adjuvanted.

HRV BAC

A cDNA clone of HRV-A16 (FIG. 1) was generated by commercial synthesis of cDNA and molecular assembly. The HRV genome and poly(A) tail are encoded by a 7199 bp cDNA. Transcription is directed by a T7 promoter (5' T7 promoter-ribozyme-HRV-A16-ribozyme-T7 terminators-3'). In vitro T7 transcription yields a 7.2 kb RNA with predicted endogenous termini due to ribozyme cleavage. The HRV capsid proteins (VP4, VP2, VP3, VP1) are flanked in the construct by SacI and ClaI restriction sites (FIG. 1). One can have cDNAs synthesized representing this capsid region for any HRV type. One can generate and rescue recombinant capsid-chimeric HRV, e.g. HRV-cap2/16 encoding the VP4, VP2, VP3, VP4, and 2A proteins of HRV-A2 and the 2B, 2C, 3A, 3C, and 3D proteins of HRV-A16 or HRV-A80.

In Vivo Testing

Four groups of mice were given either 1 HRV serotype+Alum, 3 HRV serotypes+Alum, 5 HRV serotypes+Alum, or 7 HRV serotypes+Alum (Table 4). Prior to mixing with Alum, HRV strains were completely inactivated using formaldehyde (1:4000 ratio) for 72 hours at 37° C. One hundred microliters of vaccine was injected intramuscularly per mouse. Each dose of HRVV-10 was comprised of 9 microliters of each virus stock (Table 2) inactivated, plus 10 microliters of alhydrogel, 2% aluminum hydroxide colloidal adjuvant.

TABLE 3

| Experimental Groups | HRV serotypes per group |
|---|---|
| Gr 1 (HRVV-1) | HRV-A16 |
| Gr 2 (HRVV-3) | HRV-A16 |
| | HRV-A36 |
| | HRV-A78 |
| Gr 3 (HRVV-5) | HRV-A16 |
| | HRV-A36 |
| | HRV-A78 |
| | HRV-A38 |
| | HRV-A13 |

TABLE 3-continued

| Experimental Groups | HRV serotypes per group |
|---|---|
| Gr 4 (HRVV-7) | HRV-A16 |
| | HRV-A36 |
| | HRV-A78 |
| | HRV-A38 |
| | HRV-A13 |
| | HRV-A29 |
| | HRV-B14 |

All mice were vaccinated with inactivated HRVs+alum by the intramuscular route at day 0, and sera were collected at day 18. Then, endpoint neutralizing antibody titer was measured in serum using HRVs in nAb assays. Neutralizing antibody titers to all immunized HRV strains (except HRV-A13) were observed.

50-Valent Inactivated Rhinovirus Vaccine is Broadly Immunogenic in Rhesus Macaques BALB/c mice were used to test immunogenicity. HRVs were propagated in H1-HeLa cells and inactivated infectivity using formalin. Sera from naïve mice had no detectable nAb against HRV-A16. Alum adjuvant enhanced the nAb response induced by i.m. inactivated HRV-A16 (FIG. 3). There was no effect of valency (comparing 1-, 3-, 5-, 7-, and 10-valent) on the nAb response induced by inactivated HRV-A16 or to the 3 types in the 3-valent vaccine (HRV-A16, HRV-A36, and HRV-A78) (FIG. 3). The 50% tissue culture infectious dose ($TCID_{50}$) titers of the input viruses prior to inactivation (inactivated-$TCID_{50}$) are provided.

TABLE 4

| HRV type | 1-valent | 3-valent | 5-valent | 7-valent | 10-valent |
|---|---|---|---|---|---|
| HRV-A16 | $1.7 \times 10^7$ | $3.5 \times 10^6$ | $3.5 \times 10^6$ | $3.5 \times 10^6$ | $3.2 \times 10^6$ |
| HRV-A36 | | $1.1 \times 10^7$ | $1.1 \times 10^7$ | $1.1 \times 10^7$ | $1.0 \times 10^7$ |
| HRV-A78 | | $6.3 \times 10^5$ | $6.3 \times 10^5$ | $6.3 \times 10^5$ | $5.6 \times 10^5$ |
| HRV-A38 | | | $1.1 \times 10^5$ | $1.1 \times 10^5$ | $1.0 \times 10^5$ |
| HRV-A13 | | | $6.3 \times 10^5$ | $6.3 \times 10^5$ | $5.6 \times 10^5$ |
| HRV-A29 | | | | $3.5 \times 10^4$ | $3.2 \times 10^4$ |
| HRV-B14 | | | | $3.5 \times 10^6$ | $3.2 \times 10^6$ |
| HRV-A76 | | | | | $1.9 \times 10^4$ |
| HRV-A2 | | | | | $3.2 \times 10^4$ |
| HRV-A9 | | | | | $5.6 \times 10^5$ |

Hamory et al. reported that two different 10-valent inactivated HRV preparations induced nAb titers to only 30-40% of the input virus types in recipient subjects. J Infect Dis 132, 623-629 (1975). However, the input titers of viruses prior to inactivation ranged from $10^{1.5}$ to $10^{5.5}$ $TCID_{50}$ per mL, and these were then diluted 10-fold to generate 10-valent 1.0 ml doses given i.m. as prime and boost with no adjuvant. Low input antigen doses may be responsible for poor nAb responses to 10-valent inactivated HRV. The 10-valent vaccine in Harmony was reconstituted, as closely as possible with available HRV types, over a $10^1$ to $10^5$ inactivated-$TCID_{50}$ per vaccine dose and it was compared to a 10-valent vaccine of the same types with input titers ranging from $>10^5$ to $>10^7$ inactivated-$TCID_{50}$ per dose. The Hamory vaccine resulted in no detectable nAb after prime vaccination. Following boost vaccination, nAb were detected to the five types that had the highest input titers (FIG. 3). The high titer vaccines resulted in nAb to 5 of 10 types after prime vaccination and all 10 types after the boost (FIG. 4).

Following the boost vaccinations, there appeared to be a $10^4$ inactivated-$TCID_{50}$ per vaccine dose threshold for the induction of nAb in this model (FIG. 4b). Above this titer, there was no correlation between input load and nAb induction.

Injectable vaccines used in people are commonly given in a 0.5 ml dose. The i.m. vaccine volume in mice was 0.1 mL. A 25-valent per 0.1 mL HRV vaccine was tested in mice as a scalable prototype. The 25-valent inactivated HRV vaccine had a 7.4-fold lower average inactivated-$TCID_{50}$ per type per dose than the 10-valent composition to accommodate the volume adjustment.

TABLE 5

| HRV type | 10-valent | 25-valent[1] | 25-valent[2] |
|---|---|---|---|
| HRV-A76 | $1.9 \times 10^4$ | $7.7 \times 10^3$ | $7.7 \times 10^3$ |
| HRV-A29 | $1.0 \times 10^5$ | $4.1 \times 10^4$ | $4.1 \times 10^4$ |
| HRV-A9 | $2.1 \times 10^6$ | $8.6 \times 10^5$ | $8.6 \times 10^5$ |
| HRV-B14 | $3.3 \times 10^6$ | $1.3 \times 10^6$ | $1.3 \times 10^6$ |
| HRV-A16 | $1.0 \times 10^7$ | $4.3 \times 10^6$ | $4.3 \times 10^6$ |
| HRV-A78 | $1.4 \times 10^7$ | $5.7 \times 10^6$ | $5.7 \times 10^6$ |
| HRV-A38 | $1.9 \times 10^7$ | $7.7 \times 10^6$ | $7.7 \times 10^6$ |
| HRV-A13 | $2.1 \times 10^7$ | | |
| HRV-A2 | $3.1 \times 10^7$ | $2.3 \times 10^6$ | $2.3 \times 10^6$ |
| HRV-A36 | $3.2 \times 10^7$ | $1.3 \times 10^7$ | $1.3 \times 10^7$ |
| HRV-A32 | | $2.3 \times 10^3$ | $2.3 \times 10^4$ |
| HRV-A49 | | $2.3 \times 10^4$ | $2.3 \times 10^5$ |
| HRV-A58 | | $1.2 \times 10^5$ | $2.3 \times 10^5$ |
| HRV-A55 | | $1.3 \times 10^5$ | $2.3 \times 10^6$ |
| HRV-A11 | | $1.8 \times 10^5$ | $1.8 \times 10^5$ |
| HRV-A41 | | $2.3 \times 10^5$ | $1.3 \times 10^6$ |
| HRV-A33 | | $3.2 \times 10^5$ | $2.3 \times 10^6$ |
| HRV-A39 | | $3.2 \times 10^5$ | $2.3 \times 10^6$ |
| HRV-A50 | | $3.2 \times 10^5$ | $2.3 \times 10^6$ |
| HRV-A94 | | $3.2 \times 10^5$ | $3.2 \times 10^5$ |
| HRV-A1B | | $4.1 \times 10^5$ | $1.3 \times 10^6$ |
| HRV-A21 | | $4.1 \times 10^5$ | $2.3 \times 10^6$ |
| HRV-A51 | | $4.1 \times 10^5$ | $4.1 \times 10^5$ |
| HRV-A60 | | $5.1 \times 10^5$ | $1.3 \times 10^6$ |
| HRV-B26 | | $2.3 \times 10^6$ | $2.3 \times 10^6$ |
| HRV-A45 | | $3.3 \times 10^6$ | $3.3 \times 10^6$ |

[1]Used for prime vaccination.
[2]Used for boost vaccination. In the interim between the prime and boost vaccination, we obtained higher titer virus stocks of eleven input types (bold font). Higher titers of these eleven were used in the boost vaccination.

The 10-valent inactivated HRV vaccine induced nAb to 100% of input types following the prime and the boost (FIG. 5a). The nAb induced by 10-valent inactivated HRV were persisting at 203 days post-boost. The 25-valent inactivated HRV prime vaccination induced nAb to 18 of 25 (72%) virus types, and the 25-valent boost resulted in nAb against 24 of the 25 types (96%) (FIG. 8b). The average nAb titer resulting from prime+boost was $2^7$ for 10-valent and $2^{6.8}$ for 25-valent. The data demonstrate broad neutralization of diverse HRV types with a straightforward vaccine approach.

In order to increase vaccine valency, rhesus macaques (RMs) and a 1.0 ml i.m. vaccine volume was chose. Two RMs were vaccinated with 25-valent inactivated HRV, and two RMs were vaccinated with 50-valent inactivated HRV. Pre-immune sera in RM A and RM B had no detectable nAb against the 25 HRV types included in the 25-valent vaccine. The inactivated-$TCID_{50}$ titers per dose were higher in RMs than in mice.

TABLE 6

| HRV type | 25-valent | 50-valent |
|---|---|---|
| HRV-A1B | $1.4 \times 10^7$ | $7.0 \times 10^6$ |
| HRV-A2 | $2.4 \times 10^7$ | $1.2 \times 10^7$ |
| HRV-A9 | $8.9 \times 10^6$ | $4.4 \times 10^6$ |
| HRV-A11 | $1.9 \times 10^6$ | $1.0 \times 10^6$ |
| HRV-B14 | $1.4 \times 10^7$ | $7.0 \times 10^6$ |

TABLE 6-continued

| HRV type | 25-valent | 50-valent |
|---|---|---|
| HRV-A16 | $4.4 \times 10^7$ | $2.2 \times 10^7$ |
| HRV-A21 | $2.4 \times 10^7$ | $1.2 \times 10^7$ |
| HRV-B26 | $2.4 \times 10^7$ | $1.2 \times 10^7$ |
| HRV-A29 | $4.2 \times 10^5$ | $2.1 \times 10^5$ |
| HRV-A32 | $2.4 \times 10^5$ | $1.2 \times 10^5$ |
| HRV-A33 | $2.4 \times 10^7$ | $1.2 \times 10^7$ |
| HRV-A36 | $1.4 \times 10^8$ | $7.0 \times 10^7$ |
| HRV-A38 | $8.0 \times 10^8$ | $4.0 \times 10^8$ |
| HRV-A39 | $2.4 \times 10^7$ | $1.2 \times 10^7$ |
| HRV-A41 | $1.4 \times 10^7$ | $7.0 \times 10^6$ |
| HRV-A45 | $3.7 \times 10^7$ | $1.8 \times 10^7$ |
| HRV-A49 | $2.4 \times 10^6$ | $1.2 \times 10^6$ |
| HRV-A50 | $2.4 \times 10^7$ | $1.2 \times 10^7$ |
| HRV-A51 | $4.2 \times 10^6$ | $2.1 \times 10^6$ |
| HRV-A55 | $2.4 \times 10^7$ | $1.2 \times 10^7$ |
| HRV-A58 | $2.4 \times 10^6$ | $1.2 \times 10^6$ |
| HRV-A60 | $1.4 \times 10^7$ | $7.0 \times 10^6$ |
| HRV-A76 | $2.4 \times 10^5$ | $1.2 \times 10^5$ |
| HRV-A78 | $5.9 \times 10^7$ | $2.9 \times 10^7$ |
| HRV-A94 | $3.3 \times 10^6$ | $1.6 \times 10^6$ |
| HRV-A7 | | $1.2 \times 10^6$ |
| HRV-A10 | | $1.2 \times 10^7$ |
| HRV-A13 | | $4.4 \times 10^6$ |
| HRV-A19 | | $1.4 \times 10^7$ |
| HRV-A24 | | $1.2 \times 10^7$ |
| HRV-A30 | | $1.2 \times 10^7$ |
| HRV-A31 | | $6.7 \times 10^6$ |
| HRV-A34 | | $6.7 \times 10^6$ |
| HRV-A40 | | $2.1 \times 10^6$ |
| HRV-A53 | | $1.2 \times 10^5$ |
| HRV-A54 | | $6.7 \times 10^7$ |
| HRV-A56 | | $1.2 \times 10^7$ |
| HRV-A59 | | $6.7 \times 10^6$ |
| HRV-A64 | | $1.2 \times 10^6$ |
| HRV-A66 | | $4.0 \times 10^7$ |
| HRV-A68 | | $1.6 \times 10^6$ |
| HRV-A75 | | $1.2 \times 10^7$ |
| HRV-A77 | | $2.1 \times 10^5$ |
| HRV-A80 | | $1.0 \times 10^8$ |
| HRV-A81 | | $6.7 \times 10^6$ |
| HRV-A85 | | $4.4 \times 10^7$ |
| HRV-A88 | | $1.6 \times 10^6$ |
| HRV-A89 | | $2.1 \times 10^6$ |
| HRV-A96 | | $4.4 \times 10^6$ |
| HRV-A100 | | $1.2 \times 10^7$ |

The 25-valent vaccine induced nAb to 96% (RM A) and 100% (RM B) of input viruses following the prime vaccination. The 50-valent vaccine induced nAb to 90% (RM C) and 82% (RM D) of input viruses following the prime vaccination. The breadth of nAb following prime vaccination in RM was superior to what was observed in mice, which may have been due to animal species differences and/or higher inactivated-$TCID_{50}$ input titers in the RM vaccines. Following boost vaccination, there were serum nAb titers against 100% of the types in 25-valent HRV-vaccinated RMs (FIG. 6A) and 98% (49 out of 50) of the virus types in 50-valent HRV-vaccinated RMs (FIG. 6B). The average nAb titer resulting from prime+boost in RMs was $2^{9.3}$ for 25-valent and $2^{8.6}$ for 50-valent. The nAb responses were type-specific, not cross-neutralizing, because there were minimal nAbs induced by the 25-valent vaccine against 10 non-vaccine types. The nAb response to 50-valent inactivated HRV vaccine was broad and potent in RMs.

Based on these experiments, it is estimated $10^{4.5}$ inactivated-$TCID_{50}$ per type per dose will be useful. Therefore, HRV stock titers $\geq 10^7$ $TCID_{50}$ per ml would be useful for a potential 83-valent HRV A formulation in a 0.5 ml dose containing alum adjuvant. The HRV stocks used in our vaccinations were produced in H1-HeLa cells.

The infectious yield of 10 HRV types were compared in H1-HeLa and WI-38, which can be qualified for vaccine production. Adequate yields were also obtained from WI-38 cells.

Materials and Methods

H1-HeLa (CRL-1958) and W138 (CCL-75) cells were obtained from the American Type Culture Collection (ATCC) and cultured in minimal essential media with Richter's modification and no phenol red (MEM) (ThermoFisher) supplemented with 10% fetal bovine serum. HeLa-H1 cells were tested using the LookOut Mycoplasma detection kit (Sigma), and these were mycoplasma negative. HRV-A7 (VR-1601), HRV-A9 (VR-1745), HRV-A11 (VR-1567), HRV-A13 (VR-286), HRV-B14 (VR-284), HRV-A16 (VR-283), HRV-A19 (V4-1129), HRV-A24 (VR-1134), HRV-A29 (VR-1809), HRV-A30 (VR-1140), HRV-A31 (VR-1795), HRV-A32 (VR-329), HRV-A36 (VR-509), HRV-A38 (VR-511), HRV-A40 (VR-341), HRV-A41 (VR-1151), HRV-A49 (VR-1644), HRV-A53 (VR-1163), HRV-A56 (VR-1166), HRV-A58 (VR-1168), HRV-A59 (VR-1169), HRV-A60 (VR-1473), HRV-A64 (VR-1174), HRV-A66 (VR-1176), HRV-A68 (VR-1178), HRV-A75 (VR-1185), HRV-A76 (VR-1186), HRV-A77 (VR-1187), HRV-A78 (VR-1188), HRV-A80 (VR-1190), HRV-A81 (VR-1191), HRV-A85 (VR-1195), HRV-A88 (VR-1198), HRV-A89 (VR-1199), HRV-A96 (VR-1296), and HRV-A100 (VR-1300) prototype strains were purchased from ATCC. HRV-A1B, HRV-A10, HRV-A21, HRV-B26, HRV-A33, HRV-A34, HRV-A39, HRV-A45, HRV-A50, HRV-A51, HRV-A54, HRV-A55, HRV-A94 strains were obtained from the Centers for Disease Control and Prevention. The HRVs in the study are species A, with the exception of HRV-B14, and represent A species.

HRV stocks were generated in H1-HeLa cells. Approximately 0.5 ml of HRV was inoculated onto subconfluent H1-HeLa monolayer cells in a T-182 flask. After adsorption for 1 hr at room temperature with rocking, 50 ml of HRV infection medium (MEM supplemented with 2% FBS, 20 mM HEPES, 10 mM MgCl2, 1× non-essential amino acids [Gibco catalog 11140-050]) was added and the infection was allowed to proceed at 32° C. in a 5% $CO_2$ humidified incubator until the monolayer appeared to be completely involved with cytopathic effect (CPE), 1 to 3 days post-infection. The cells were scraped, and the cells and medium (approximately 50 ml) were transferred to two pre-chilled 50 ml conical polypropylene tubes and kept on ice while each suspension was sonicated using a Sonic Dismembrator Model 500 (Fisher Scientific) equipped with a ½-inch diameter horn disrupter and ¼-inch diameter tapered microtip secured on a ring stand. Sonication was performed by an operator in a closed room with ear protection, at 10% amplitude, 1 sec on/1 sec off intervals, and 1 pulse per 1 ml of material. Sonication yielded higher titers than freeze-thaw. The suspension was clarified by centrifugation at 931×g for 10 minutes. The supernatant was transferred to cryovials, snap-frozen in liquid nitrogen, and stored at −80° C. For comparing HRV yield in H1-HeLa and WI-38 cells, T-75 flasks of subconfluent cells were infected at a multiplicity of infection (MOI) of 0.1 $TCID_{50}$/cell, and 20 ml of culture medium were discarded prior to scraping the cells in the remaining 5 ml followed by sonication. For stocks, $TCID_{50}$/ml titers were determined by infecting subconfluent H1-HeLa cells in 96-well plates with serially diluted samples, staining the cells six days post-infection with 0.1% crystal violet/20% methanol, scoring wells for CPE, and calculating the endpoint titer using the Reed and Muench method a reported in: "A simple method of estimating fifty percent endpoints." Am J Hyg 27, 493-497 (1938).

HRV stock was harvested from H1-HeLa cell monolayers as describe above and clarified by brief centrifugation at low speed to remove large cellular debris (931×g, 10 min, 4° C.). In order to remove excess albumin from the crude virus stock by affinity chromatography, the supernatant was loaded onto a HiTrap Blue HP column (GE Healthcare) using an ÄKTAPurifier system (GE Healthcare) according to the manufacturer specifications. Flowthrough was subsequently loaded through a HiTrap Capto Core 700 column (GE Healthcare) to refine the virus prep by size exclusion chromatography (SEC). The flowthrough from the HiTrap Blue HP and the HiTrap Capto Core 700 was captured using the ÄKTAPurifier system (GE Healthcare) with a 20 mM sodium phosphate buffer (pH 7.0). Flowthrough from SEC was dialyzed overnight with 0.1 M Tris-HCl buffer (pH 8.0), then loaded onto a HiTrap Q XL column (GE Healthcare) and separated into fractions by ion exchange chromatography. Virus-containing fractions were eluted using the ÄKTAPurifier system (GE Healthcare) with a 0.1 M Tris-HCl buffer (pH 8.0) and a sodium chloride gradient. Fractions showing high absorption peaks at 280 nM were collected and analyzed for viral titer by $TCID_{50}$ end-point dilution assay, and fraction purity visualized on a 10% SDS-PAGE gel by silver stain (Thermo Fisher Scientific). Fractions of HRV-A16, HRV-A36, and HRV-A78 of high virus titer and purity were combined for formalin-inactivation as described below.

Young adult (3-5 kg, 2-4 years of age, 2 females and 2 males) Indian rhesus macaques (*Macaca mulatta*; RM) were allocated in an un-blinded fashion to two vaccine groups (25-valent and 50-valent), one male and one female per group. Before immunization, all HRV types were inactivated by addition of 0.025% formalin followed by incubation with stirring for 72 hr at 37° C. Complete inactivation of infectivity was confirmed by end-point $TCID_{50}$ titration in H1-HeLa cells. Formalin inactivation by this method resulted in greater immunogenicity in mice than alternative inactivation by beta-propiolactone, suggesting formalin inactivation preserved antigenic determinants. Mice were vaccinated i.m. with inactivated HRV strains mixed with 100 μg of Alhydrogel adjuvant 2% (aluminum hydroxide wet gel suspension, alum) (Sigma catalog A8222 or Invivogen catalog vac-alu) according instructions of the manufacturers. The total volume per mouse was 100 μL, administered in 50 μL per thigh. Mice were given a second identical vaccination (boost) at the time. RMs were vaccinated i.m. with inactivated HRV strains mixed with 500 μg of Alhydrogel adjuvant 2%. The total volume per RM was 1 ml, administered in one leg. RMs were boosted with an identical vaccination at four weeks.

In mice, peripheral blood was collected into microcentrifuge tubes from the submandibular vein. Samples were incubated at room temperature for 20 min to clot. The tubes were centrifuged 7500×g for 10 min to separate serum. The serum samples were pooled from mice of each group and stored at −80° C. until used. Phlebotomy involving RMs was performed under either ketamine (10 mg/kg) or Telazol (4 mg/kg) anesthesia on fasting animals. Following anesthesia with ketamine or Telazol, the animals were bled from the femoral vein. After collecting blood in serum separating tube (SST), samples were incubated at room temperature for 30 min. The tubes were centrifuged 2500×g for 15 min to separate serum. The serum samples from individual RM were stored at −80° C. until used.

H1-HeLa cells were seeded in 96-well plates to attain 80-90% confluence in 24 h. Heat-inactivated (56° C., 30 min) serum samples were 2-fold serially diluted in MEM and added to 500 $TCID_{50}$/mL HRV of each type to be tested, in an equal volume. The virus and serum mixtures were incubated 37° C. for 1 h. Then, 50 μL of the serum-virus mixture was transferred onto H1-HeLa cell monolayers in 96-well plates in triplicate, and plates were spinoculated at 2,095×g for 30 min at 4° C. For each type, a no-serum control was added to test the input 500 $TCID_{50}$. We tested pooled HRV-A16 anti-sera against HRV-A16 in each assay as a standard. After spinoculation, 150 μL of HRV infection medium were added to each well. The 96-well plates were incubated for 6 days at 32° C. and 5% $CO_2$ and then stained with crystal violet as described above. Wells were scored for the presence or absence of CPE. Neutralizing antibody endpoint titers and 95% confidence intervals were determined by the method of Reed and Muench. The 95% confidence interval indicates variability of three technical replicates within a single nAb experiment.

The invention claimed is:

1. A vaccine composition comprising 25 or more inactivated human rhinovirus (HRV) serotypes including rhinoviruses of the following serotypes: HRV-A16, HRV-A36, HRV-A78, HRV-A38, HRV-A2, HRV-B14, HRV-A9, HRV-A29, HRV-A76, HRV-A60, HRV-A49, HRV-A41, HRV-A32, HRV-A58, and HRV-A11 and an adjuvant comprising aluminum hydroxide, aluminum phosphate, potassium aluminum sulfate, or mixtures thereof.

2. A method of preventing a human rhinovirus infection comprising administering an effective amount of prime and boost vaccine, wherein the prime and boost composition each comprises comprising 25 or more inactivated human rhinovirus (HRV) serotypes including rhinoviruses of the following serotypes: HRV-A16, HRV-A36, HRV-A78, HRV-A38, HRV-A2, HRV-B14, HRV-A9, HRV-A29, HRV-A76, HRV-A60, HRV-A49, HRV-A41, HRV-A32, HRV-A58, and HRV-A11, and an adjuvant comprising aluminum hydroxide, aluminum phosphate, potassium aluminum sulfate, or mixtures thereof, to a subject in need thereof.

3. The method of claim 2 wherein the prime dose of vaccine is administered and the boost dose is administered more than 3 days after the prime dose.

4. The method of claim 2, wherein the subject is less than five years of age.

5. The method of claim 2, wherein the subject is greater than 60 years of age.

6. The method of claim 2, wherein the subject is diagnosed with asthma, COPD, emphysema, chronic bronchitis, or cystic fibrosis.

7. A method of preventing a human rhinovirus infection comprising administering an effective amount of prime and boost vaccine, wherein the prime and boost composition each comprises comprising inactivated human rhinovirus (HRV) serotypes: HRV-A76, HRV-A29, HRV-A9, HRV-B14, HRV-A16, HRV-A78, HRV-A38, HRV-A2, HRV-A36, HRV-A32, HRV-A49, HRV-A58, HRV-A55, HRV-A11, HRV-A41, HRV-A33, HRV-A39, HRV-A50, HRV-A94, HRV-A1B, HRV-A21, HRV-A51, HRV-A60, HRV-B26, and HRV-A45, and wherein each serotype is at a concentration of greater than $1 \times 10^3$ $TCID_{50}$ per mL, and an adjuvant comprising aluminum hydroxide, aluminum phosphate, potassium aluminum sulfate, or mixtures thereof, to a subject in need thereof.

8. The method of claim 7, wherein the prime dose of vaccine is administered and the boost dose is administered more than 3 days after the prime dose.

9. The method of claim 7, wherein the subject is less than five years of age.

10. The method of claim 7, wherein the subject is greater than 60 years of age.

11. The method of claim 7, wherein the subject is diagnosed with asthma, COPD, emphysema, chronic bronchitis, or cystic fibrosis.

12. A method of preventing a human rhinovirus infection comprising administering an effective amount of prime and boost vaccine, wherein the prime and boost composition each comprises comprising inactivated human rhinovirus (HRV) serotypes: HRV-A1B, HRV-A2, HRV-A9, HRV-A11, HRV-B14, HRV-A16, HRV-A21, HRV-B26, HRV-A29, HRV-A32, HRV-A33, HRV-A36, HRV-A38, HRV-A39, HRV-A41, HRV-A45, HRV-A49, HRV-A50, HRV-A51, HRV-A55, HRV-A58, HRV-A60, HRV-A76, HRV-A78, HRV-A94, HRV-A7, HRV-A10, HRV-A13, HRV-A19, HRV-A24, HRV-A30, HRV-A31, HRV-A34, HRV-A40, HRV-A53, HRV-A54, HRV-A56, HRV-A59, HRV-A64, HRV-A66, HRV-A68, HRV-A75, HRV-A77, HRV-A80, HRV-A81, HRV-A85, HRV-A88, HRV-A89, HRV-A96, and HRV-A100, and wherein each serotype is at a concentration of greater than $1 \times 10^4$ $TCID_{50}$ per mL, and an adjuvant comprising aluminum hydroxide, aluminum phosphate, potassium aluminum sulfate, or mixtures thereof, to a subject in need thereof.

13. The method of claim 12, wherein the prime dose of vaccine is administered and the boost dose is administered more than 3 days after the prime dose.

14. The method of claim 12, wherein the subject is less than five years of age.

15. The method of claim 12, wherein the subject is greater than 60 years of age.

16. The method of claim 12, wherein the subject is diagnosed with asthma, COPD, emphysema, chronic bronchitis, or cystic fibrosis.

17. A vaccine composition comprising inactivated human rhinovirus (HRV) serotypes: HRV-A76, HRV-A29, HRV-A9, HRV-B14, HRV-A16, HRV-A78, HRV-A38, HRV-A2, HRV-A36, HRV-A32, HRV-A49, HRV-A58, HRV-A55, HRV-A11, HRV-A41, HRV-A33, HRV-A39, HRV-A50, HRV-A94, HRV-A1B, HRV-A21, HRV-A51, HRV-A60, HRV-B26, and HRV-A45, wherein each serotype is at a concentration of greater than $1 \times 10^3$ $TCID_{50}$ per mL, and an adjuvant comprising aluminum hydroxide, aluminum phosphate, potassium aluminum sulfate, or mixtures thereof, to a subject in need thereof.

18. A vaccine composition comprising inactivated human rhinovirus (HRV) serotypes: HRV-A1B, HRV-A2, HRV-A9, HRV-A11, HRV-B14, HRV-A16, HRV-A21, HRV-B26, HRV-A29, HRV-A32, HRV-A33, HRV-A36, HRV-A38, HRV-A39, HRV-A41, HRV-A45, HRV-A49, HRV-A50, HRV-A51, HRV-A55, HRV-A58, HRV-A60, HRV-A76, HRV-A78, HRV-A94, HRV-A7, HRV-A10, HRV-A13, HRV-A19, HRV-A24, HRV-A30, HRV-A31, HRV-A34, HRV-A40, HRV-A53, HRV-A54, HRV-A56, HRV-A59, HRV-A64, HRV-A66, HRV-A68, HRV-A75, HRV-A77, HRV-A80, HRV-A81, HRV-A85, HRV-A88, HRV-A89, HRV-A96, and HRV-A100, wherein each serotype is at a concentration of greater than $1 \times 10^4$ $TCID_{50}$ per mL, and an adjuvant comprising aluminum hydroxide, aluminum phosphate, potassium aluminum sulfate, or mixtures thereof, to a subject in need thereof.

* * * * *